US011266476B1

(12) United States Patent
Willis et al.

(10) Patent No.: US 11,266,476 B1
(45) Date of Patent: Mar. 8, 2022

(54) HEADGEAR STORAGE DEVICE AND METHOD OF DISTRIBUTION

(71) Applicant: Forest Devices, Inc., Pittsburgh, PA (US)

(72) Inventors: Dan Willis, Pittsburgh, PA (US); Carmelo Montalvo, Pittsburgh, PA (US); Andrew Martin, Smithtown, NY (US)

(73) Assignee: Forest Devices, Inc., Pittsburgh, PA (US)

( * ) Notice: Subject to any disclaimer, the term of this patent is extended or adjusted under 35 U.S.C. 154(b) by 0 days.

(21) Appl. No.: 17/224,176

(22) Filed: Apr. 7, 2021

(51) Int. Cl.
| *A61B 50/30* | (2016.01) |
| *A61B 5/266* | (2021.01) |
| *A61B 5/256* | (2021.01) |
| *A61B 5/00* | (2006.01) |
| *G07F 9/00* | (2006.01) |
| *G06Q 20/08* | (2012.01) |

(52) U.S. Cl.
CPC .............. *A61B 50/30* (2016.02); *A61B 5/256* (2021.01); *A61B 5/266* (2021.01); *A61B 5/72* (2013.01); *G06Q 20/085* (2013.01); *G07F 9/002* (2020.05); *A61B 5/6803* (2013.01)

(58) Field of Classification Search
CPC ........ A61B 50/30; A61B 5/6803; G07F 9/002
See application file for complete search history.

(56) References Cited

U.S. PATENT DOCUMENTS

| 3,474,775 | A | 10/1969 | Johnson |
| 3,508,541 | A | 4/1970 | Westbrook et al. |
| 3,602,216 | A | 8/1971 | Moe, Jr. et al. |
| 3,776,228 | A | 12/1973 | Semler |
| 4,458,687 | A | 7/1984 | Dickson |
| 4,632,122 | A | 12/1986 | Johansson et al. |
| 4,742,831 | A | 5/1988 | Silvian |
| 4,919,148 | A | 4/1990 | Muccio |
| 5,078,134 | A | 1/1992 | Heilman et al. |
| 5,479,934 | A | 1/1996 | Imran |
| 5,689,215 | A | 11/1997 | Richardson et al. |
| 6,301,493 | B1 | 10/2001 | Marro et al. |
| 6,510,333 | B1 | 1/2003 | Licata et al. |
| 6,516,218 | B1 | 2/2003 | Cheng et al. |
| 6,574,513 | B1 | 6/2003 | Collura et al. |

(Continued)

FOREIGN PATENT DOCUMENTS

CN          103720470 A       4/2014

*Primary Examiner* — John P Lacyk (74) *Attorney, Agent, or Firm* — Buchanan Ingersoll & Rooney PC (57) ABSTRACT

Apparatuses for storage and distribution of headgear having sensors and a gel distribution apparatus can be configured to permit storage of the headgear while also protecting the gel distribution modules of the headgear from being inadvertently actuated for deployment of gel to avoid unintended gel leaks or gel applications. In some embodiments, the storage apparatus can be sized and configured to fit within a vending machine for providing remote distribution of the headgear while also protecting the headgear from damage during falls that can occur when the vending machine is activated to distribute a headgear to a customer. Methods of distributing the headgear can utilize an embodiment of the storage device and/or use of at least one vending machine or a network of vending machines.

20 Claims, 7 Drawing Sheets

(56) References Cited

U.S. PATENT DOCUMENTS

| | | |
|---|---|---|
| 6,640,122 B2 | 10/2003 | Manoli et al. |
| 6,952,605 B1 | 10/2005 | Scarberry |
| 7,367,956 B2 | 5/2008 | King |
| 7,474,918 B2 | 1/2009 | Frantz et al. |
| 7,490,054 B2 * | 2/2009 | Reade .................. G06Q 20/20 705/16 |
| 7,941,213 B2 | 5/2011 | Markowitz et al. |
| 8,265,736 B2 | 9/2012 | Sathaye et al. |
| 8,444,559 B2 | 5/2013 | Fink et al. |
| 8,663,121 B2 | 3/2014 | Stickney et al. |
| 9,305,418 B2 * | 4/2016 | Feuer .................. G07F 7/10 |
| D831,115 S * | 10/2018 | Chambers .................. D20/1 |
| 10,872,489 B1 * | 12/2020 | Carter .................. G06Q 20/18 |
| 2007/0255127 A1 | 11/2007 | Mintz et al. |
| 2007/0272313 A1 | 11/2007 | Olds |
| 2008/0009763 A1 | 1/2008 | Chiou et al. |
| 2010/0036275 A1 | 2/2010 | Alkire |
| 2010/0137708 A1 | 6/2010 | Tamura et al. |
| 2011/0245707 A1 | 10/2011 | Castle et al. |
| 2012/0022349 A1 | 1/2012 | Poupko et al. |
| 2012/0107811 A1 | 5/2012 | Kelso et al. |
| 2012/0143020 A1 | 6/2012 | Bordoley et al. |
| 2013/0023748 A1 | 1/2013 | Afanasewicz et al. |
| 2014/0142410 A1 | 5/2014 | Erb et al. |
| 2014/0243643 A1 | 8/2014 | Sunderland |
| 2015/0065838 A1 | 3/2015 | Wingeier et al. |
| 2015/0112153 A1 | 4/2015 | Nahum |
| 2015/0313498 A1 | 11/2015 | Coleman et al. |
| 2016/0022165 A1 | 1/2016 | Sackellares et al. |
| 2016/0022981 A1 | 1/2016 | Wingeier et al. |
| 2016/0144186 A1 | 5/2016 | Kaemmerer et al. |
| 2016/0235322 A1 | 8/2016 | Alkire |
| 2016/0287127 A1 | 10/2016 | Kesinger et al. |
| 2016/0346534 A1 | 12/2016 | Isaacson et al. |
| 2017/0281036 A1 | 10/2017 | Parvizi et al. |
| 2018/0165923 A1 | 6/2018 | Schmit et al. |
| 2019/0021664 A1 | 1/2019 | Kesinger et al. |
| 2020/0237248 A1 | 7/2020 | Willis et al. |

\* cited by examiner

S1  Fold headgear and place within storage device 11 so gel receptacles are within gel receptacle cavities 15b of recesses 15 defined in the case 10.

S2  Close and seal storage device 11 after headgear 1 is positioned therein

S3  Transport headgear 1 retained in storage devices 11 to one or more remote distribution devices 30 for storage therein.

S4  Actuate remote distribution devices 30 to receive storage device 11 having headgear 1 therein after providing payment via the user interface 33.

S5  Open storage device 11 and connect headgear 1 to a computer device.

S6  Refer to instructions included in storage device 11 for positioning and/or use of the headgear 1.

FIG. 9

HEADGEAR STORAGE DEVICE AND METHOD OF DISTRIBUTION

FIELD

The present innovation relates to devices that can be utilized to store and/or distribute headgear having a gel distribution apparatus incorporated therein. The present innovation also relates to methods of making and using such devices and distributing such storage devices containing one or more headgears.

BACKGROUND

A headband in which electrodes are in fixed positions can be used to position electrodes on the head of a patient. The electrodes are often intended to be placed so they will fall in all the positions described in the 10/20 montage. Other headgear in which electrodes can be included are disclosed in U.S. Patent Application Publication Nos. 2019/0021664, 2016/0235322 and 2010/0036275. Electrode configurations and uses can also be appreciated from U.S. Patent Application Publication Nos. 2020/0237248, 2017/0281036, 2016/0346534, 2016/0287127, 2016/0144186, 2016/0022981, 2015/0313498, 2015/0112153, 2014/0142410, 2014/0243643, 2013/0023748, 2012/0143020, 2012/022349, 2011/0245707, 2010/0137708, 2007/0272313, and 2007/0255127 and U.S. Pat. Nos. 3,474,775, 3,602,216, 3,776,228, 4,458,687, 4,742,831, 4,919,148, 5,689,215, 6,516,218, 6,640,122, 6,952,605, 7,367,956, 7,474,918, 7,616,980, 7,941,213, 8,265,736, 8,444,559, and 8,663,121.

SUMMARY

We have determined that headgear having sensors can have significant storage and distribution problems. For example, after a single use of headgear, the headgear must be washed or otherwise cleaned for a subsequent use. As another example, application of gel during the use of the headband can require significant cleaning of the headgear to be performed to remove the applied gel that may get adhered to the headgear or absorbed into the headgear. Moreover, we determined that there is no easy way to provide for storage of headgear for a user such as a care provider to be able to easily obtain a new headgear and then utilize that headgear while a prior used headgear is cleaned or thrown away. Instead, repeated use of the same headgear is often contemplated and the control of that headgear by one or more specialized doctors to provide a centralized authority over use and cleaning of the headgear is typically required.

We have developed solutions to help mitigate against such issues. For example, a headgear can be stored and distributed to permit the headgear to be a single use headgear or a headgear that can be recycled for subsequent use in a way that permits a decentralized distribution of the headgear to end users. Some embodiments of this distribution system can utilize remote vending machines that can be refilled when the headgear items are detected as being low in the vending machine or the vending machine is detected as having no more headgear to provide to an end user.

Moreover, we contemplate that the end user for headgear can be an emergency care provider (e.g. medic who may provide emergency care after arriving to see a patient in an emergency situation via an ambulance or other type of ambulatory vehicle). Such an emergency care provider may operate independently of doctors to provide first responder emergency care at homes or other residences of a patient and then transport that patient to a particular care facility (e.g. a medic for supplying an ambulance, etc.). Such personnel can operate independently from hospitals and may need a different, less centralized approach for obtaining new headgear suitable for use by the first responder. In particular, we determined that it can be beneficial for such personnel to be able to obtain new headgear after a first use of an old headgear via a remote headgear distribution device (e.g. a vending machine type device) to permit such personnel to easily replace used headgear with new headgear without having to undertake any cleaning of the previously used headgear. The old headgear can be trash or can be recycled for cleaning and reuse via use of a recycle receptacle for the headgear or via use of a trashcan for the old headgear being replaced with the new headgear obtainable via the remote headgear distribution device. The remote headgear distribution device in which new headgear can be stored for subsequent distribution to such personnel can be located in or near emergency rooms to permit such personnel to easily replenish their supply of headgear on an ad hoc, as needed basis.

Some headgear in use can often require use of a gel to help improve the connection sensors of the electrodes of the headgear may have to a patient's head for providing reliably good measurements of a patient's condition. Embodiments of the storage apparatus we have developed can permit a compact storage of headgear that also permits a gel distribution apparatus to be incorporated into the stored headgear and stored in the apparatus without a risk of inadvertent application of gel or gel leakage or at least a significant reduction in the risk of such an occurrence that could arise from transport or distribution of the headgear.

A storage device for headgear is provided. Embodiments of the storage device can be for headgear that is configured to be connected to a computer device to measure biosignals of a patient for evaluation of a neurological condition of the patient. The storage device can include a case having a bottom, a top, and at least one sidewall that define a headgear retaining cavity. The bottom of the case can define a floor within the case between the at least one sidewall and the bottom and between the bottom and the top. The floor can have a plurality of recesses. Each of the recesses can have at least one recess wall that extends from the floor to define a gel receptacle cavity sized and configured to receive a gel receptacle of a respective gel distribution module of a gel distribution apparatus of the headgear.

The storage device can be configured in some embodiments so that at least one recess wall of each of the recesses is positioned so that at least one flange of the gel distribution module is positionable adjacent the recess wall outside of the gel receptacle cavity to contact the floor when the headgear is within the headgear retaining cavity in a folded storage position.

The top can be moveably connected to the at least one sidewall and be moveable so that the storage device is adjustable between an open position and a closed position. For example, the top can be hingedly connected to one of the at least one sidewall. In other embodiments, the top can be removable from the at least one sidewall or be slideably to open the top. In yet other embodiments, the top can be slideable or resiliently moveable about the at least one sidewall.

In some embodiments, the top can be translucent and can have a label attached thereto. The label can have a front side and a back side. The back side of the label can include instructional indicia and the front side of the label including headgear name indicia. The instruction indicia can be viewable through the translucent top.

Embodiments of the storage device can include wrapping that is positioned around the case. The wrapping can be opaque or translucent. In some embodiments, the wrapping can be a polymeric film. In other embodiments, the wrapping can be paper, tape, another type of wrapping material or combinations thereof.

The at least one sidewall of the storage device can have at least one sidewall recess. Each sidewall recess can have at least one recess wall that extends from the sidewall to define a gel receptacle cavity sized and configured to receive a gel receptacle of a respective gel distribution module of a gel distribution apparatus of the headgear when the headgear is within the retaining cavity in a folded storage position.

In yet other embodiments of the storage device, the storage device can include all of the above noted features or only a subset of these features.

A distribution system for headgear is also provided. The distribution system can be configured for a headgear that is to be connected to a computer device to measure biosignals of a patient for evaluation of a neurological condition of the patient. The distribution system can include headgear having a flexible body positionable between a folded storage position and a use position. The headgear can have a gel distribution apparatus. The system can also include a storage device. The storage device can include an embodiment of the above mentioned storage device or another type of storage device. For instance, the storage device can include a case having a bottom, a top, and at least one sidewall that define a headgear retaining cavity. The bottom of the case can define a floor within the case between the at least one sidewall and the bottom and between the bottom and the top. The floor can have a plurality of recesses. Each of the recesses can have at least one recess wall that extends from the floor to define a gel receptacle cavity that is sized and configured to receive a gel receptacle of a respective gel distribution module of the gel distribution apparatus of the headgear when the headgear is in the folded storage position and is within the headgear retaining cavity.

Embodiments of the distribution system can also include other features. For example, a remote distribution device configured to store the storage device in a closed position with the headgear stored within the headgear retaining cavity while the headgear is in the folded storage position can be included. The remote distribution device can include an interface to receive user input for payment for the headgear and an output mechanism. The storage device can be removable from the remote distribution device via the output mechanism. The output mechanism includes a door, a moveable tray, or other type of access opening from which a user can grab a storage device case after having paid for the headgear. In some embodiments, the remote distribution device can include an actuator configured to move the storage device to a bottom portion of the remote distribution device adjacent the output mechanism in response to receipt of payment for the headgear stored within the storage device. The use can then take the storage device from the remote distribution device via the output mechanism.

The storage device of the distribution system can include an above discussed embodiment of the storage device or other embodiment of the storage device discussed herein. In some embodiments of the storage device of the system. The at least one sidewall can have at least one sidewall recess. Each sidewall recess can have at least one recess wall that extends from the sidewall to define a gel receptacle cavity sized and configured to receive a gel receptacle of a respective gel distribution module of a gel distribution apparatus of the headgear when the headgear is within the headgear retaining cavity in a folded storage position. The distribution system can be configured so that the headgear is configured such that all gel distribution modules of the gel distribution apparatus have their gel receptacles within a respective gel receptacle cavity of a respective one of the recesses when the headgear is within the headgear retaining cavity in the folded storage position.

A method of distributing headgear is also provided. Embodiments of the method can utilize an embodiment of the storage device and/or distribution system. Embodiments of the method can include providing headgear having a flexible body and a gel distribution apparatus attached to the body, folding the body of the headgear to position the headgear in a folded storage position, positioning the headgear in the folded storage position within a headgear retaining cavity of a case of a storage device such that each gel receptacle of the gel distribution apparatus is within a respective gel receptacle cavity of the case when the headgear is in the folded storage position and is within the headgear retaining cavity, and closing the storage device.

Embodiments of the method can also include other steps. For instance, the method can also include positioning the storage device having the headgear within the headgear retaining cavity in a remote distribution device. As another example, the method can also (or alternatively) include receiving payment for the headgear via an interface of the remote distribution device and, in response to receiving the payment, the remote distribution device permitting the storage device having the headgear within the headgear retaining cavity to be removed from the remote distribution device. As yet another example, embodiments of the method can also include manipulating an output mechanism of the remote distribution device; to remove the remote distribution device.

Embodiments of the storage device can be utilized in embodiments of the method. In some embodiments, the case of the storage device can include a plurality of gel receptacle recesses having gel receptacle cavities in a floor of the case. The case can also include a plurality of gel receptacle recesses having gel receptacle cavities in at least one sidewall of the case. When the headgear is within the headgear retaining cavity, flanges of each gel distribution module can be outside of a respective gel receptacle to contact the floor around that receptacle while a gel receptacle is within the gel receptacle cavity of the gel receptacle recess.

Other details, objects, and advantages of apparatuses for storage and distribution of headgear having sensors and a gel distribution apparatus, and methods of making and using the same will become apparent as the following description of certain exemplary embodiments thereof proceeds.

BRIEF DESCRIPTION OF THE DRAWINGS

Exemplary embodiments of apparatuses for storage and distribution of headgear having sensors and a gel distribution apparatus and methods of making and using the same are shown in the accompanying drawings. It should be understood that like reference numbers used in the drawings may identify like components.

DETAILED DESCRIPTION

Referring to FIGS. 1-9, an exemplary embodiment of headgear 1 can have a sensor array 24 included in a body 2. The body 2 can be comprised of fabric or a fabric type material. For example, the body can be formed from cotton, polyester, cotton and polyester blended fabric, nylon, flax, rayon, viscose, material composed of regenerated cellulose fibers, wool, bamboo, texliner mesh, hemp, leather, fish leather, lyocell, another other type of fabric material or textile type material and combinations thereof. The body 2 can alternatively be composed of a semi-rigid plastic in some less preferred embodiments.

Figure 1:
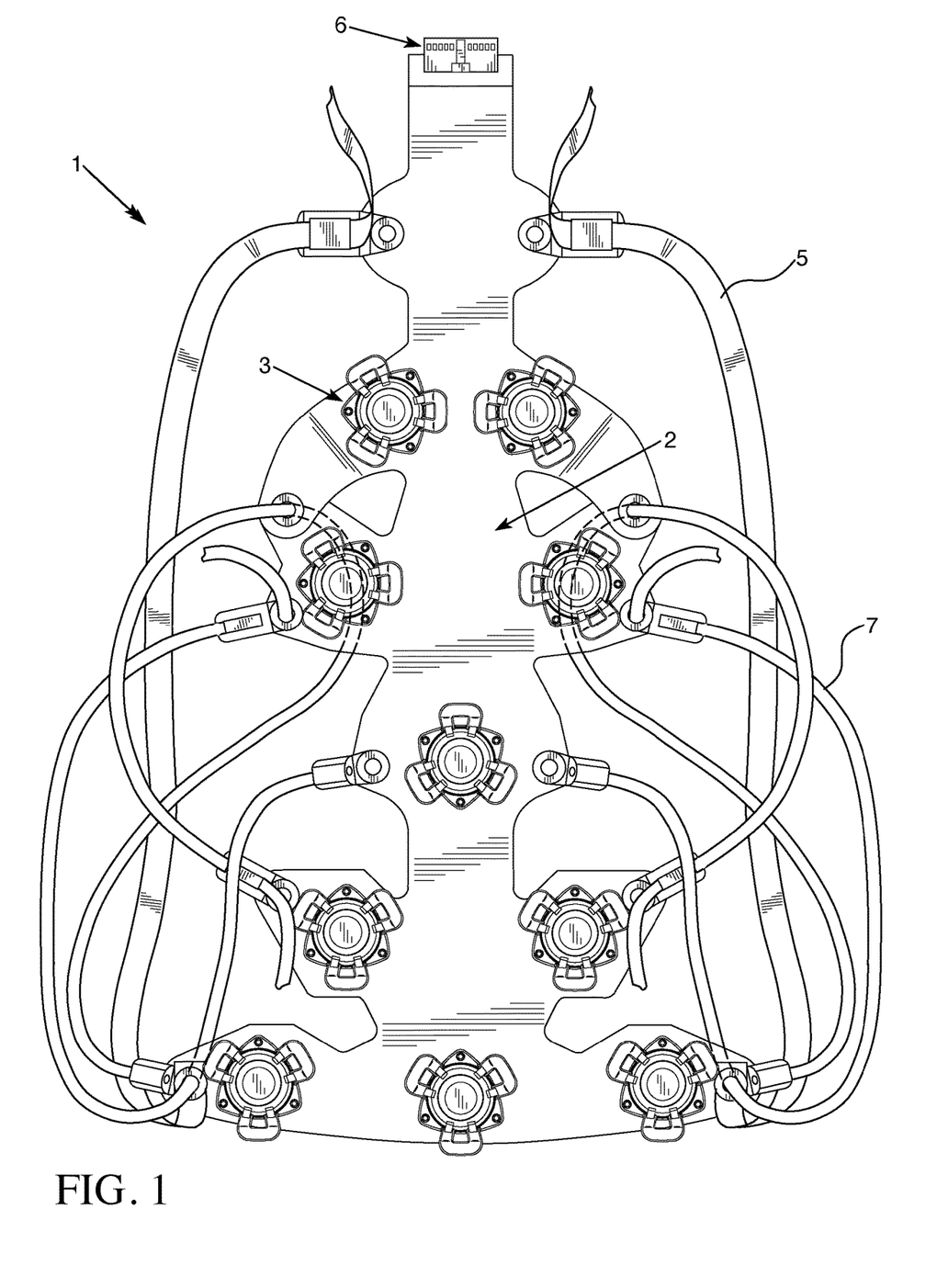
FIG. 1 is a perspective top view of a first exemplary embodiment of headgear having an exemplary embodiment of a gel distribution apparatus that includes gel distribution modules 3 attached to the body 2 of the headgear 1. The headgear 1 can be folded and stored in a storage device such as, for example, the exemplary storage device shown in FIGS. 4-8.
Figure 3:
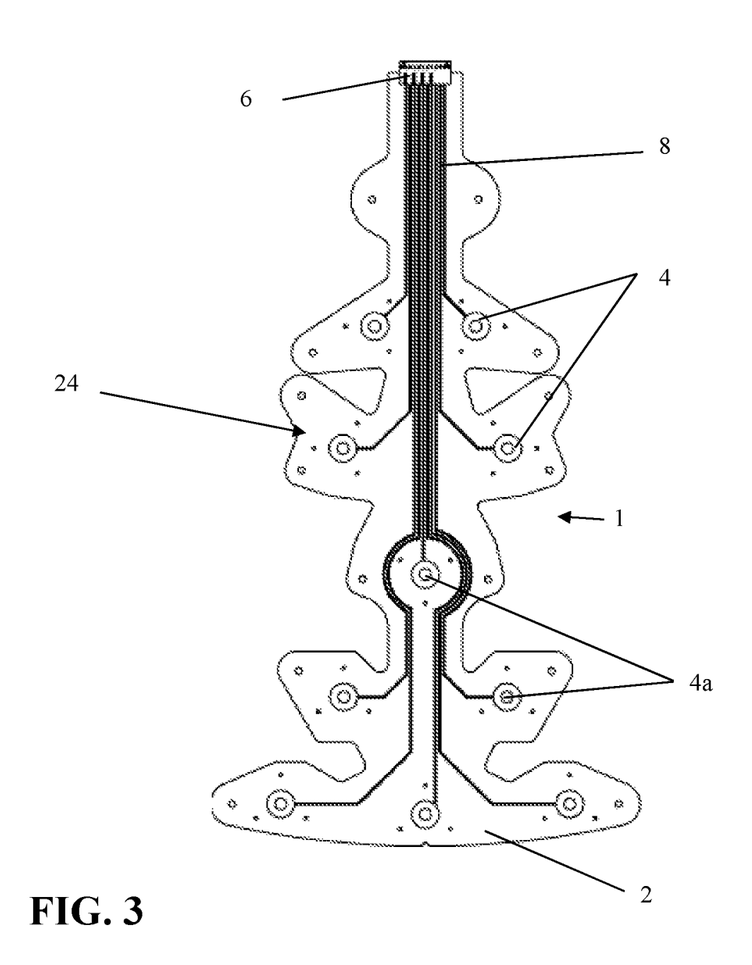
FIG. 3 is a bottom view of the body 2 of the first exemplary embodiment of headgear 1 illustrating sensors 4 of a sensor array 24, conductive connectors 8, and a communication connector 6 of the headgear 1.

The body 2 can include conductive connectors 8. Each conductive connector 8 can be comprised of a body that is structured as an elongated member that is composed of metal or other electrically conductive material that can convey an electrical signal and/or other data from the sensor(s) to which that conductive connector 8 is attached to a communication connector 6 for transmission of the signal and/or other data of a sensor 4 of sensor array 24 to a computer device (e.g. a neurological condition detection unit, a stroke detection device, etc.). The computer device can be configured to evaluate the data from the sensor array and evaluate whether the patient has undergone a stroke or has experienced another type of neurological injury.

Each conductive connector 8 can have at least two terminal ends—a first terminal end and a second terminal end opposite the first terminal end. The communication connector 6 can be attached to first terminal ends of the conductive connectors 8 adjacent to or at a rear of the body 2 that is opposite the front of the body 2. The communication connector 6 can be a separate element connected to first terminal ends of the conductive connectors 8 to facilitate a connection with wiring, cabling, or other communication connection device (e.g. transceiver unit, a universal serial bus ("USB") connection, etc.). In some embodiments, it is contemplated that fabric material of the body 2 can be hardened to define the communication connector 6 at the rear of the body at which first terminal ends of the conductive connectors 8 are positioned for connection to another element. Each conductive connector 8 can be positioned on the body 2 so that its second terminal end can be connected to a respective sensor 4 (e.g. terminating at the sensor, conductively connected to the sensor, etc.).

Each sensor 4 can be configured as an electrode or other type of sensor (e.g. a detector) that can detect and/or measure brain waves of a patient or other biosignals of a patient. The sensor 4 can have a body that has an annular shape that includes an inner hole 4a or can be a non-annular structure (e.g. a disc, a plate, etc.).

In some embodiments the communication connector 6 can be used in conjunction with a security chip to prevent fraudulent copies of the head gear from being improperly utilized. In another embodiment, the communication connection 6 can be used with a security chip or identification chip to prevent unauthorized use and/or record the number of uses of the sensor array 24 or headgear 1.

Figure 2:
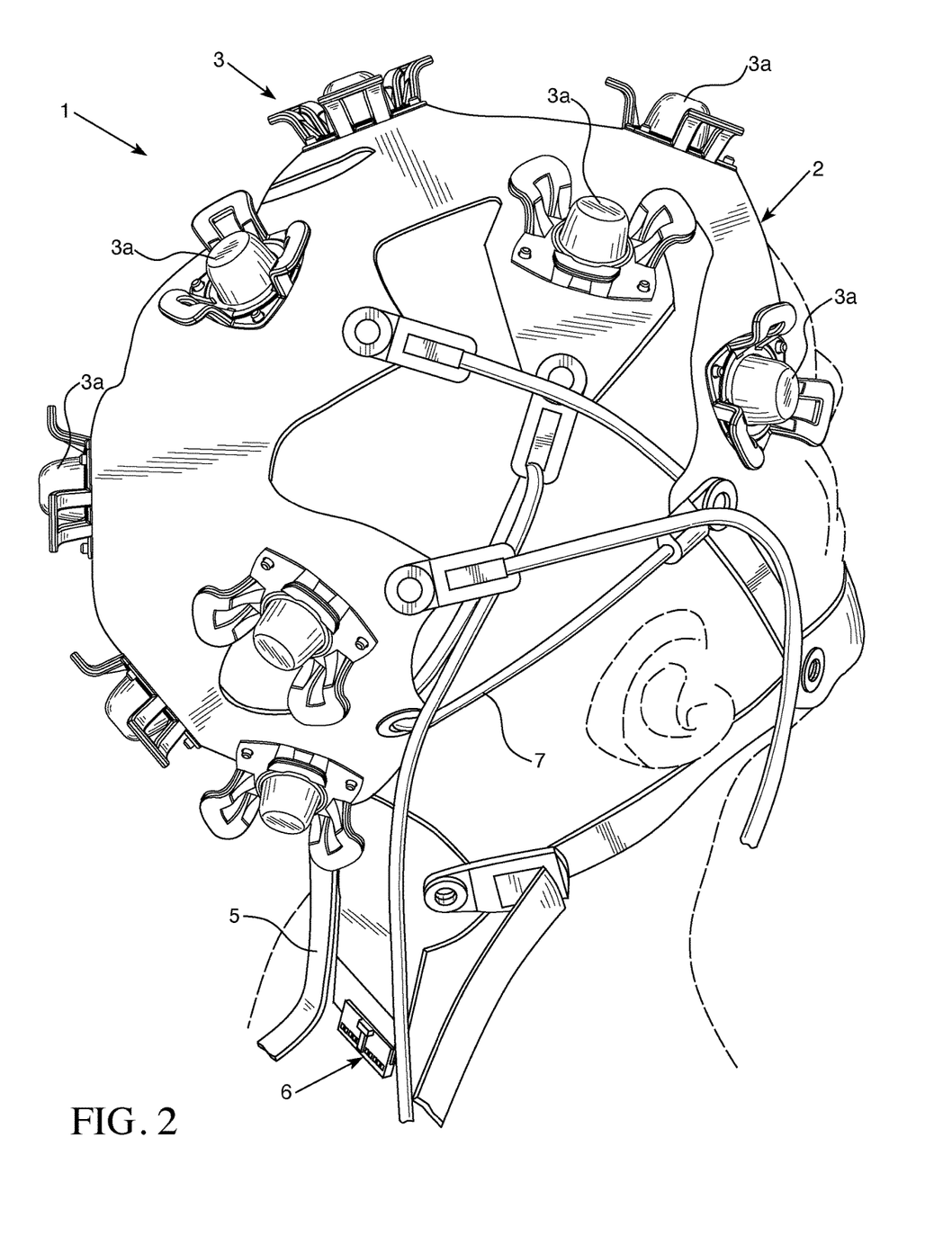
FIG. 2 is a perspective view of the first exemplary embodiment of the headgear 1 being worn by a patient after it is taken out of the storage device for use.

The body 2 of the headgear 1 can be configured so that it is wearable on the head of a patient. FIG. 2 illustrates an example of a patient wearing the headgear 1 on the patient's head. The headgear 1 can include straps 7 and other types of elongated elements, such as cords 5, to help position the headgear on the patient's head and sufficiently tighten the headgear on the head so that the sensors 4 can be placed into contact with the scalp of the patient's head or be positioned adjacent to the patient's scalp (e.g. within a millimeter (mm) of being in contact with the patient's scalp, within 4 mm of contacting the patient's scalp, within 6 mm of contacting the patient's scalp, etc.). The headgear can also include a chin strap that is attached to the body 2 for providing a tight connection with the patient's chin for helping to position and sufficiently tighten the headgear 1 on the patient's head for positioning of the sensors in pre-selected positions about the patient's head for measuring biosignal data or other health metric data from the patient via the sensors 4 so that such measurement data obtained by the sensors 4 can be provided to at least one computer device via the conductive connectors 8 and communication connector 6 communicatively connected to the sensors 4. The computer device can then utilize that data to evaluate at least one medical condition of the patient.

The body 2 of the headgear 1 can have sensors 4 positioned on an internal side of the body 2 that is to be directly contacting the head of a patient when the patient wears the headgear. The opposite side of the body 2 can be an external side that is opposite the internal side. The external side can face away from the patient's head when the headgear is worn on the patient's head. The sensor array 24 can include a plurality of sensors 4. Each sensor 4 can be connected to a respective one of the conductive connectors 8 so that measurement data collected by the sensor can be transmitted to the communication connector 6 for sending to at least one computer device connected to the communication connector 6 (e.g. there can be a respective conductive connector for a respective one of the sensors 4 of the sensor array 24).

The headgear 1 can also include a gel distribution apparatus that includes a plurality of gel distribution modules 3. The gel distribution modules can include a first gel distribution module, second gel distribution module, third gel distribution module, a fourth gel distribution module, as well as other gel distribution modules such that there is a respective gel distribution module for each sensor 4 of the sensor array 24 or at least a gel distribution module for a preselected number of the sensors 4 of the sensor array 24.

For example, there can be a respective gel distribution module 3 that is attached to or otherwise adjacently positioned to a respective sensor 4 of the sensor array 24 so that each sensor 4 has its own respective gel distribution module 3. Each gel distribution module 3 can be a device configured to store gel and facilitate the output of the stored gel onto the scalp of a patient's head and/or onto the sensor 4 to which the gel distribution module is attached or otherwise adjacently positioned to help facilitate the formation of a sufficiently strong electrical connection between the sensor and the patient's scalp to help ensure that the sensor can obtain measurement data from the patient of a sufficiently high quality. The gel can be can be a silver chloride gel (e.g. an AgCl gel, a mixture that includes AgCl and water that forms a gel or slurry at room temperature, etc.). The gel could alternatively be another type of electrical conduction connection enhancement gel.

As may best be seen from FIGS. 4-8, the body 2 of the headgear 1 can be designed and configured to be folded from a use position in which the headgear is positionable for being worn on the head of a patient to a folded storage position that positions the headgear 1 for storage within a headgear retaining cavity 13 of a case 10 of a storage device 11. For example, after being fabricated, the body 2 can be moved from a use position to the folded storage position for storage within a headgear storage device 11. The body 2 of the headgear can be folded into its folded storage position such that the body 2 of the headgear is adjusted in size to relatively compactly fit within the headgear retaining cavity 13 and be fully enclosed within that cavity after the storage device 11 is moved from its open position to its closed position.

Figure 4:
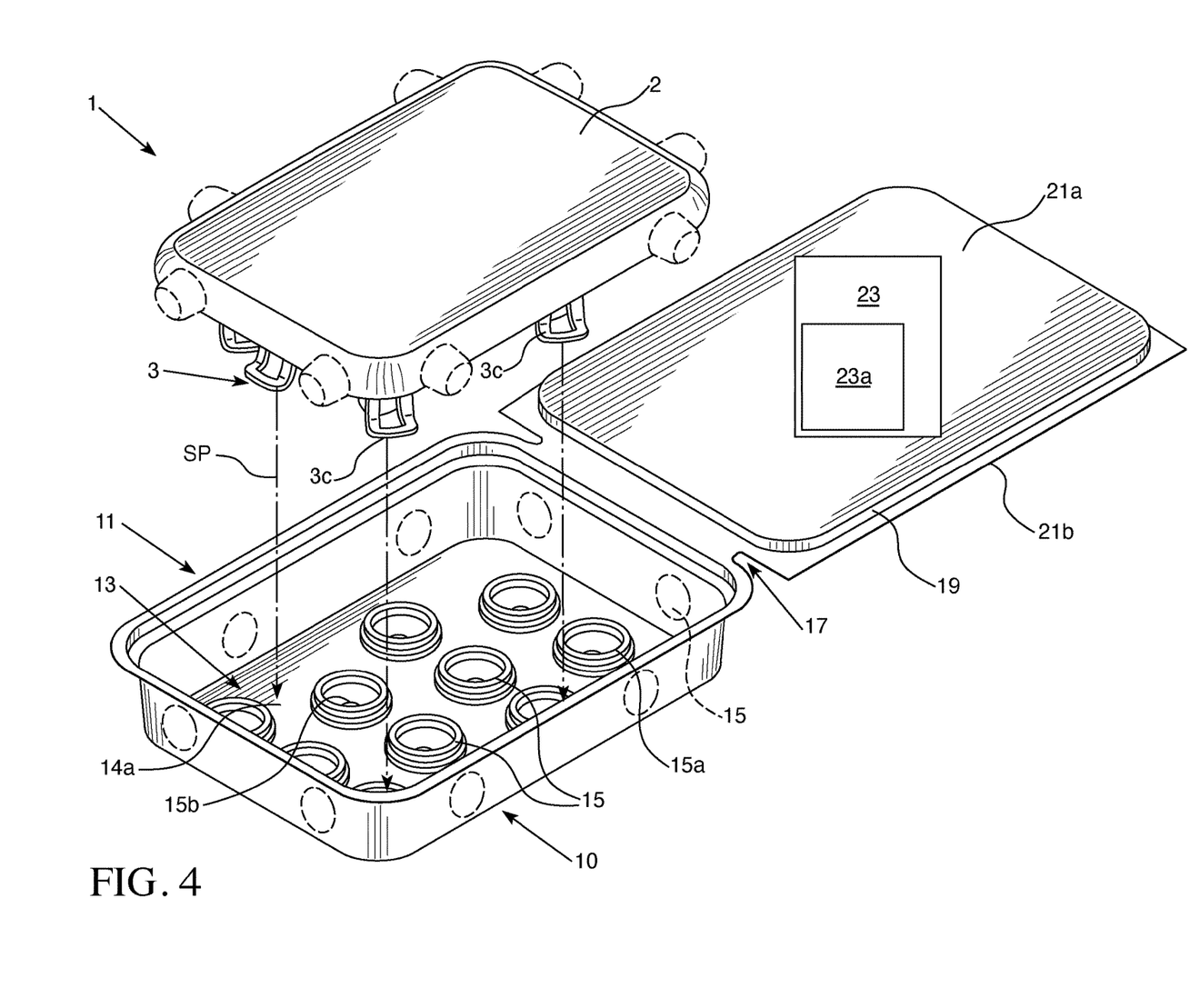
FIG. 4 is a perspective view of a first exemplary storage device in an open position to receive and store the first exemplary embodiment of the headgear 1 in a folded storage position. An optional configuration of the headgear 1 can also be appreciated from the gel distribution modules 3 shown in broken line in FIG. 4, which are shown as having their gel receptacles and flanges extending in different sideward directions (e.g. left, right, front, and rear sides) in addition to a first sideward direction (e.g. a downward direction) shown by the solid line gel distribution modules.

In the folded storage position, the body 2 can be positioned so that the gel receptacles 3a that retain gel within a gel reservoir defined therein and/or flanges 3c for all the gel modules of the gel distribution apparatus of the headgear can extend away from the body 2 of the headgear in the same direction for storage in the headgear retaining cavity 13 of the case 10. In other embodiments, the gel receptacles 3a and the flanges 3c of a first set of modules can extend away from the body 2 in a first direction (e.g. a downward direction as shown in FIG. 4), a second set of the modules can have their receptacles 3a and flanges 3c extend in a second direction away from the body (e.g. a first sideward direction in which the flanges 3c and gel receptacles 3a extend toward a first side of a first sidewall 13a of the case 10 of the storage device 11) when the body 2 is in its folded storage position for storage in the case 10. In yet other embodiments, the gel receptacles 3a and the flanges 3c of a first set of gel distribution modules can extend away from the body 2 in a first direction (e.g. a downward direction as shown in FIG. 4 in which flanges 3c and gel receptacles extend toward the floor 14a of the case 10), a second set of the gel distribution modules can have their receptacles 3a and flanges 3c extend in a second direction away from the body (e.g. a first sideward direction in which the flanges 3c and gel receptacles 3a extend toward a first side of a first sidewall 13a of the case 10 of the storage device 11), and a third set of the gel distribution modules 3 can have their receptacles 3a and flanges 3c extend in a third direction away from the body (e.g. a second sideward direction that is opposite the first sideward direction in which the flanges 3c and gel receptacles 3a extend toward a second side of the case 10 of the storage device 11 when the body 2 is in its folded storage position for storage. In yet other embodiments, the body 2 can be configured so that when it is in the folded storage position for storage the gel receptacles 3a and the flanges 3c of a first set of gel distribution modules can extend away from the body 2 in a first direction (e.g. a downward direction as shown in FIG. 4), a second set of the gel distribution modules have their receptacles 3a and flanges 3c extend in a second direction away from the body (e.g. a first sideward direction in which the flanges 3c and gel receptacles 3a extend toward a first side of a first sidewall 13a of the case 10 of the storage device 11), a third set of the gel distribution modules 3 have their receptacles 3a and flanges 3c extend in a third direction away from the body (e.g. a second sideward direction that is opposite the first sideward direction in which the flanges 3c and gel receptacles 3a extend toward a second side of the case 10 of the storage device 11), a fourth set of the gel distribution modules 3 have their gel receptacles 3a and flanges 3c extend in a fourth direction away from the body (e.g. a third sideward direction that is perpendicular to the first sideward direction and is also perpendicular to the second sideward direction in which the flanges 3c and gel receptacles 3a extend toward a front of the case 10 of the storage device 11), and a fifth set of the gel distribution modules have their gel receptacles 3a and flanges 3c extend in a fifth direction away from the body (e.g. a fourth sideward direction that is perpendicular to the first sideward direction and is also perpendicular to the second sideward direction and is also opposite the third sideward direction in which the flanges 3c and gel receptacles 3a extend toward a rear of the case 10 of the storage device 11).

It should be appreciated that for embodiments of the body 2 of the headgear 1 in which there are multiple sets of gel distribution modules that have their gel receptacles and flanges 3c extending in different directions away from the body 2 when the body 2 is in its folded storage position, one or more of the different sets of gel distribution modules may only include a single gel distribution module 3 while other sets may include multiple gel distribution modules 3. In yet other embodiments, all the sets can include multiple gel distribution modules.

The bottom 14b of the case 10 can define a floor 14a of the headgear retaining cavity 13. The floor can be positioned within the case 10 between the sidewalls 13a and the bottom, between the different sidewalls 13a of the left, right, front and rear sides of the case 10, and also be between the bottom 14b and the top 19 of the case 10. The floor 14a can have a plurality of recesses 15 defined therein. Each of the recesses 15 can be defined by one or more internal recess walls 15a that extend from the floor 14a to define a gel receptacle cavity 15b sized to receive the gel receptacle 3a of a respective one of the gel distribution modules 3. In other embodiments, the recesses 15 can be defined by gel receptacle cavities 15b that are defined in the floor 14a to create deeper depressions within the floor for receiving gel receptacles 3a that extend from the gel distribution modules 3 of the headgear 1.

Each of the gel receptacle cavities 15b of the case 10 can be sized so that the flanges 3c that extend beyond the gel receptacle 3a and around a periphery of the gel receptacle 3a can contact the floor 14a adjacent to the one or more recess walls 15a defining the gel receptacle cavity 15b and/or adjacent the gel receptacle cavity 15b while being outside of that cavity. Each gel receptacle cavity 15b can be sized so that there is a gap between the gel receptacle 3a and the bottom of the gel receptacle cavity 15b when the one or more flanges 3c that are around the periphery of the gel receptacle contact the floor 14a adjacent the recess wall(s) 15a that define the gel receptacle cavity 15b. This gap can permit the headgear 1 to be further compressed while in its folded storage position such that the flanges 3c contact the floor 14a during storage and may further resiliently move without the gel receptacles 3a contacting the structure of the case 10 defining the bottom of the gel receptacle cavity 15b or by only permitting a minimal amount of contact between the gel receptacle 3a and the structure of the case 10 defining the bottom of the gel receptacle cavity 15b to help avoid an excessive amount of force being applied to the gel receptacle 3a to avoid the gel receptacle from inadvertently rupturing and, as a result, leaking gel that is retained therein.

For embodiments in which the body 2 is in a folded storage position for storage in the headgear retaining cavity 13, the body can be positioned so that there can also be gel receptacles 3a and one or more flanges 3c that extend in a second sideward direction, third sideward direction, fourth sideward direction, and/or fifth sideward direction as mentioned above, the one or more sidewalls 13a can have similar recesses 15 (shown in broken line in FIG. 4) defined therein for receiving the gel receptacles 3a of those modules within a defined gel receptacle cavity 15b while the one or more flanges extend to and contact the sidewall around the recess. These gel receptacle cavities 15b can also be defined so that the gel receptacle 3a of the module retainable therein avoids contact with a portion of the sidewall 13a that defines the distal end of the gel receptacle cavity 15b within that sidewall 13a.

Figures 5, 6, 7:
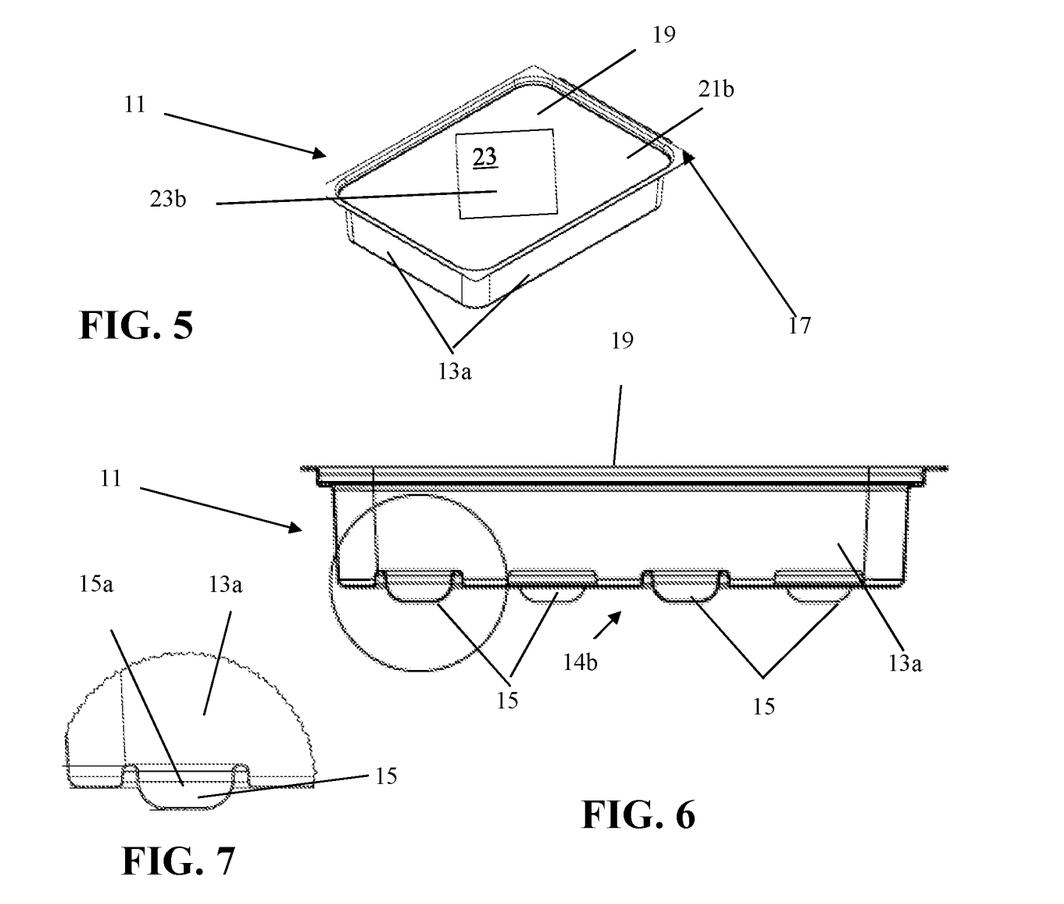
FIG. 5 is a perspective view of a first exemplary storage device in a closed position.
FIG. 6 is a side view of the first exemplary storage device in a closed position.
FIG. 7 is an enlarged view of the portion of the first exemplary storage device in a closed position that is circled in FIG. 6.

The storage device 11 can include a case 10 that has a base portion that has a bottom 14b that defines a floor 14a of a headgear storage cavity 13 defined in the case 10. The case 10 can also include at least one sidewall 13a that extends from the bottom 14b of the case for enclosing the sides of the case 10 and a top 19 that can be moveably connected to at least one sidewall 13a so that the top 19 of the case 10 can be moved relative to the sidewalls 13a and bottom 14b of the case. 10 to move the storage device from a closed position for enclosing the headgear retaining cavity 13 defined by the one or more sidewalls 13a and bottom 14b and an open position for exposing the headgear retaining cavity 13. In some embodiments, the top 19 can be considered a lid that can be hingedly or resiliently connected to a sidewall 13a for movement between open and closed positions for opening and closing the case 10. In other embodiments, it is contemplated that the top 19 can be detachably connectable to one or more of the sidewalls 13a for enclosing the headgear retaining cavity 13 via a resilient snap connection or mateable connection between the top 19 and at least one sidewall 13a or multiple sidewalls 13a that help define the headgear retaining cavity 13. The top 19 can include at least one label 23 positioned therein. The label 23 can include a front side 23b, which can include indicia to identify the headgear stored within the headgear retaining cavity 13 (e.g. headgear name indicia, etc.). The front side 23b can face outwardly from the outward side 21b of the top 19 when the storage device is in its closed position. The back side 23a of the label 23 can be positionable for facing toward the opposite inward side 21a of the top 19 and can face toward the floor 14a of the case 10 when the top 19 is in a closed position. The back side 23a of the label 23 can include text, drawings, and other indicia that can provide instructions for position and/or use of the headgear 1 to be stored in the headgear retaining cavity 13. The label 23 can be positioned within the top 19 or on the outer side 21b of the top 19 and the top 19 can be composed of a translucent material so a user can simply read both the front and back sides of the label 23 when the top 19 is in its open position. In other embodiments, the label can be on the outer side 21b of the top and be openable and/or unfoldable to view the back 23a of the label to read the instructions. In such embodiments, the top can be composed of an opaque material that blocks light from passing into the headgear retaining cavity. Sidewalls 13a and bottom 14b can be composed of an opaque material or a translucent material. For embodiments in which exposure to light or sunlight can degrade material of the headgear, a wrapping positioned over the case 10 can be opaque or the sidewalls 13a, bottom 14b, and top 19 can be opaque to block the undesired light.

Once the storage device 11 has been moved to its open position, had the headgear 1 placed within the headgear retaining cavity 13 and subsequently been moved to its closed position via movement of the top 19 to fully enclose the headgear within the headgear retaining cavity 13 of the case 10, the storage device 11 can be further sealed by wrapping the case in a wrapper. The wrapping can include one or more polymeric films of polymeric wrapping being positioned over the storage device in its closed position to help further seal the top 19 for enclosure of the case 10 and help ensure the headgear 1 is stored in a sterile, air-tight manner.

Figure 8:
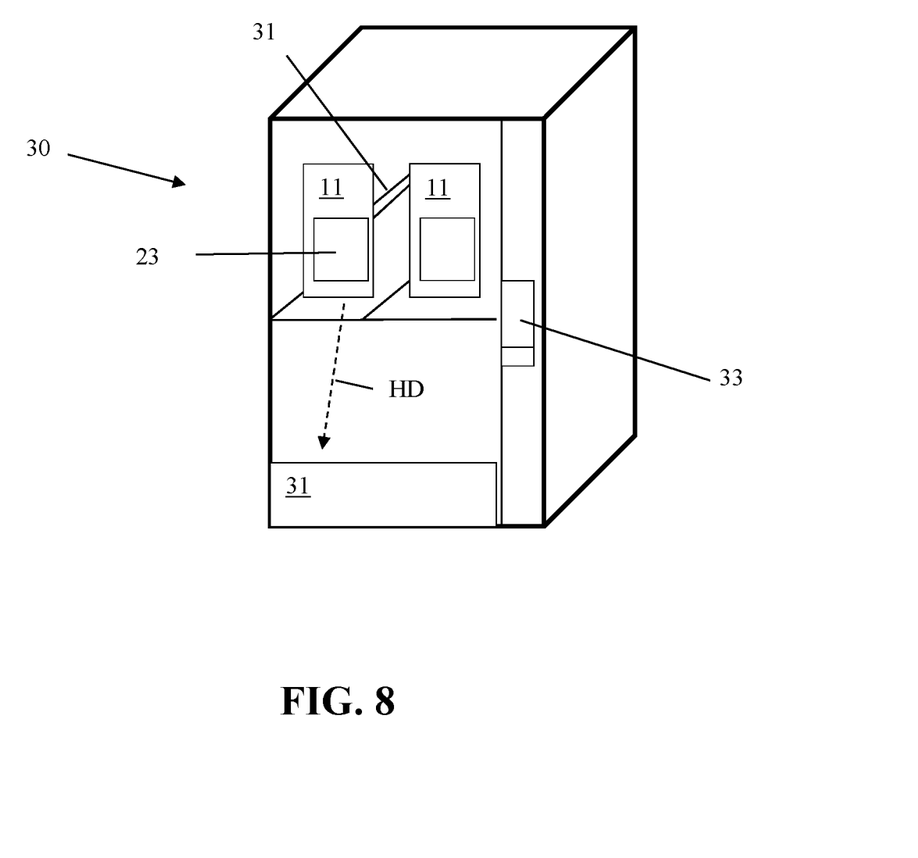
FIG. 8 is a schematic view of an exemplary distribution system that utilizes a remote distribution device for distributing one or more headgears 1 stored within storage device 11 after receipt of payment via an interface 33 of the remote distribution device 30.

As may best be seen in FIG. 8, the storage device 11 can be sized to fit within one or more shelves or racks of a remote distribution device 30, which can be configured as a vending machine device or a vending machine type device. The remote distribution device 30 can be a vending machine that is sized to be positioned in or near a hospital emergency care area of a hospital in a room that first responder personnel who convey patients to or from a hospital emergency room may pass through. The remote distribution device 30 can be plugged in to a wall outlet within the room for being powered and can include a housing that has a user interface 33 that can include buttons and a payment interface that is configured to receive money or credit card information for payment for one or more storage devices 11 to be output from the machine to a user. The remote distribution device can also include an output mechanism 31, such as a drawer, a moveable door, or other structure that can permit a user to open an enclosure of the remote distribution device 30 to take the one or more paid for storage devices 11 that retain headgear 1 therein. A user can use the interface 33 to press one or more buttons or a touch screen display to select the number of headgear 1 within storage devices 11 to be purchased to actuate the remote distribution device's controller to cause an actuator 31 to move the stored storage device(s) 11 of a shelf or rack in a headgear delivery direction HD for dropping the storage device into a bottom portion of the machine near the output mechanism 31 so that the user can receive the storage device(s) 11 having the headgear 1 that were purchased from the output mechanism 31 (e.g. opening a door to grab the storage device 11 and remove it from within the remote distribution machine 30 after the storage device 11 is dropped to the bottom area of the machine). In other configurations, the output mechanism 31 can be a door that is openable to access the inside of the machine so a user can manually take the purchased headgear within the storage device 11 before closing the door of the machine to complete the transaction for obtaining the headgear 1. Once the user has removed the storage device 11 from the machine, he or she can remove any wrapping and then open the storage device 11 by moving the top 19 to remove the headgear 1 from within the headgear retaining cavity 13.

After opening the storage device 11 and removing the headgear 1, the user can connect the headgear 1 to a computer device via the communication connector 6 and use the headgear to obtain data from a patient for evaluating a medical condition of the patient. Examples of the computer device 6 can include a computer device disclosed in U.S. Pat. Nos. 10,456,059 or 10,420,505.

The user can also use the gel distribution modules 3 to apply gel to the head of the patient prior to using the headgear 1 to collect health metric data from the patient. The application of the gel can be performed after the headgear 1 is on the patient's head by manipulating the gel receptacles 3a of the gel distribution modules 3 to push gel out of the gel receptacles 3a and onto the scalp of the patient. The application of the gel can help improve the electrical connection between the patient's head and the sensors of the headgear 1. After the application of the gel, the user can then use the computer device and sensors to measure biosignals of the patient for evaluation of a medical condition of a patient (e.g. detect whether the patient has experienced a stroke or other type of neurological injury).

The user can be a first responder that may provide emergency care to a patient at their home or office or other location after arriving to care for the patient in an ambulatory vehicle. The headgear 1 can be removed from the storage device 11 that was purchased or otherwise obtained from a remote distribution device 30 after the care provider is with the patient so that the headgear 1 can be taken out of the case 10 and put on the patient's head for connecting to a computer device. This can occur inside or outside of the ambulatory vehicle. After the headgear 1 is used to evaluate the condition of the patient, the ambulatory vehicle can transport the patient to a suitable care facility. For example, if a stroke is detected via the headgear 1 and computer device, the first responder can drive the ambulatory vehicle to route the patient to a hospital that has a specific specialization for caring for patients who have experienced a stroke. After delivering the patient to the hospital, the care provider may throw away the used headgear 1 or place it in a recycling container that may store used headgear until they can be subsequently cleaned and sterilized and have a new gel distribution apparatus attached to the body 2 for a subsequent repackaging of the headgear 1 in a new storage device 11 for recycling of the headgear 1.

After or before disposing of the used headgear 1, the user can stop at a remote distribution device 30, use the interface 33 to pay for a new headgear 1 stored in a storage device 11, remove that purchased headgear 1 within the storage device 11 obtained from the remote distribution device 30 via the output mechanism 31 after paying for the headgear 1, and then store the storage device 11 in the ambulatory vehicle so that the storage device 11 can be opened and the new headgear 1 can be used in the future when providing care to a new patient requiring emergency care. The storage device 11 can be stored in an ambulatory vehicle (e.g. an ambulance) to await such a future use.

The provider of the headgear 1, a hospital, or other care provider can replenish the supply of headgear 1 within storage devices 11 in the remote distribution devices 30 when the devices are low on storage devices 11 holding headgear 1 or out of storage devices 11 retaining the headgear 1. This can allow an ad hoc distribution of the headgear 1 that can help minimize logistical and delivery complexities by simplifying the distribution process for the headgear 1 while also avoiding a need to have to clean headgear 1 for reuse of the headgear 1.

Figure 9:
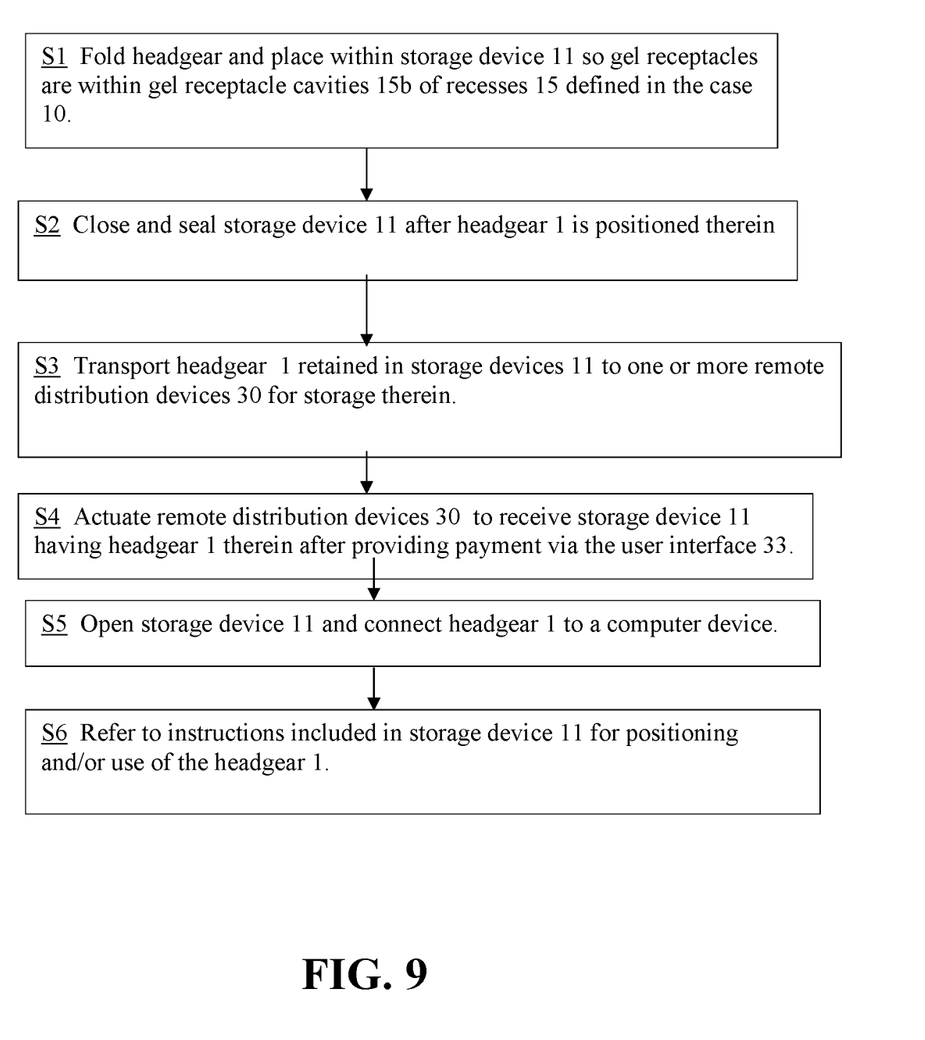
FIG. 9 is a flow chart illustrating an exemplary method of using at least one exemplary embodiment of the storage device for distribution of headgear for use in connection with a computer device used to evaluate a medical condition of a patient.

As may be appreciated from FIG. 9, there are a number of other headgear distribution methods that can be employed. For example, in a first step S1 headgear that is fabricated can be folded into its folded storage position and placed within a storage device so gel receptacles 3a are within recesses defined in the case of the storage device. The storage device can then be closed after the headgear is positioned therein in a second step S2. The headgear 1 can be transported in their storage devices 11 to a vending machine or other type of remote distribution device for storage therein in a third step S3. Thereafter, the remote distribution device 30 can be actuated via payment using the interface 33 and permit a user to obtain a storage device 11 retaining the headgear 1 from the machine via an output mechanism 31 in a fourth step S4. The user can then open the storage device 11 and connect the headgear 1 to a computer device in a fifth step S5. The user may refer to instructions included in the storage device 11 for positioning and/or use of the headgear for use of the headgear to collect data from the patient for evaluation of a medical condition of the patient in a sixth step S6. Thereafter, the patient's condition can subsequently be evaluated by a computer device connected to the headgear so that the patient's condition can be determined for routing of the patient to an appropriate care facility in one or more subsequent steps. After delivery of the patient to the appropriate care facility, the used headgear 1 can be disposed of and a new headgear 1 can be obtained from a remote distribution device 30 as discussed herein. When the remote distribution device 30 is detected as being low or out of headgear, it can be replenished for subsequent use.

There can be a network of remote distribution devices 30 positioned throughout a region (e.g. at different care facilities, etc.). Each of the remote distribution devices can be independently monitored for low levels of headgear 1 so that new headgear can be obtained and positioned in the remote distribution devices 30 for refilling the devices 30. The monitoring can occur by periodic supply checks of different remote distribution devices 30 or can be performed automatically by a sensor of the remote distribution device 30 that can trigger the transmission of a replenishment alert to a supplier to trigger resupplying of the remote device. Such a transmission of a replenishment alert can be performed via an internet connection the remote distribution device 30 may have to a local area network of the building in which it is positioned or via another type of communication connection the remote distribution device may have to a communication device of the supplier. The resupply of the remote distribution devices 30 can be controlled by the headgear provider 1, a care facility, or other distributor who may purchase the headgear 1 in storage devices 11 for sale via the remote distribution devices 30.

It should be appreciated that different embodiments of an apparatuses for storage and/or distribution of headgear having sensors and a gel distribution apparatus can utilize different arrangements to meet a particular set of design criteria. For instance, the sensors 4 and collapsible gel distribution modules of the gel distribution apparatus can have bodies of different shapes (e.g. polygonal shaped, oval shaped, dome shaped, etc.). As another example, the size, shape, and configuration of the flanges of the gel distribution modules can be different from the exemplary arrangements shown in the drawings (e.g. there can be more than three flanges, only two flanges, only a single flange, the one or more flanges can have a different shape or geometry, etc.)

and the storage device for such a headgear can be configured to facilitate storage of that particular design of the headgear.

As yet another example, it should be appreciated that some components, features, and/or configurations may be described in connection with only one particular embodiment, but these same components, features, and/or configurations can be applied or used with many other embodiments and should be considered applicable to the other embodiments, unless stated otherwise or unless such a component, feature, and/or configuration is technically impossible to use with the other embodiment. Thus, the components, features, and/or configurations of the various embodiments can be combined together in any manner and such combinations are expressly contemplated and disclosed by this statement. Therefore, while certain exemplary embodiments of apparatuses for storage and distribution of headgear having sensors and a gel distribution apparatus and methods of making and using the same have been shown and described above, it is to be distinctly understood that the invention is not limited thereto but may be otherwise variously embodied and practiced within the scope of the following claims.

What is claimed is:

1. A storage device for headgear configured to be connected to a computer device to measure biosignals of a patient for evaluation of a neurological condition of the patient, the storage device comprising:
a case having a bottom, a top, and at least one sidewall that define a headgear retaining cavity, the bottom defining a floor within the case between the at least one sidewall and the bottom and between the bottom and the top, the floor having a plurality of recesses, each of the recesses having at least one recess wall that extends from the floor to define a gel receptacle cavity sized and configured to receive a gel receptacle of a respective gel distribution module of a gel distribution apparatus of the headgear.

2. The storage device of claim 1, wherein the at least one recess wall of each of the recesses is positioned so that at least one flange of the gel distribution module is positionable adjacent the recess wall outside of the gel receptacle cavity to contact the floor when the headgear is within the headgear retaining cavity in a folded storage position.

3. The storage device of claim 1, wherein the top is hingedly connected to one of the at least one sidewall.

4. The storage device of claim 1, wherein the top is translucent and has a label attached thereto, the label having a front side and a back side, the back side of the label including instructional indicia and the front side of the label including headgear name indicia.

5. The storage device of claim 1, comprising:
wrapping that is positioned around the case.

6. The storage device of claim 1, wherein the top is moveably connected to the at least one sidewall and is moveable so that the storage device is adjustable between an open position and a closed position.

7. The storage device of claim 1, wherein the top is releaseably attached to the at least one sidewall so that the storage device is adjustable between an open position and a closed position.

8. The storage device of claim 1, wherein the at least one sidewall has at least one sidewall recess, each sidewall recess having at least one recess wall that extends from the sidewall to define a gel receptacle cavity sized and configured to receive a gel receptacle of a respective gel distribution module of a gel distribution apparatus of the headgear when the headgear is within the headgear retaining cavity in a folded storage position.

9. An apparatus for storage of headgear configured to be connected to a computer device to measure biosignals of a patient for evaluation of a neurological condition of the patient, the apparatus comprising:
headgear having a flexible body positionable between a folded storage position and a use position, the headgear having a gel distribution apparatus;
a storage device, the storage device comprising:
a case having a bottom, a top, and at least one sidewall that define a headgear retaining cavity, the bottom defining a floor within the case between the at least one sidewall and the bottom and between the bottom and the top, the floor having a plurality of recesses, each of the recesses having at least one recess wall that extends from the floor to define a gel receptacle cavity that is sized and configured to receive a gel receptacle of a respective gel distribution module of the gel distribution apparatus of the headgear when the headgear is in the folded storage position and is within the headgear retaining cavity.

10. The apparatus of claim 9, comprising:
a remote distribution device configured to store the storage device in a closed position with the headgear stored within the headgear retaining cavity while the headgear is in the folded storage position, the remote distribution device including an interface to receive user input for payment for the headgear and an output mechanism, the storage device being removable from the remote distribution device via the output mechanism.

11. The apparatus of claim 10, wherein the output mechanism includes a door.

12. The apparatus of claim 10, wherein the remote distribution device includes an actuator configured to move the storage device to a bottom portion of the remote distribution device adjacent the output mechanism in response to receipt of payment for the headgear stored within the storage device.

13. The apparatus of claim 10, wherein the at least one sidewall has at least one sidewall recess, each sidewall recess having at least one recess wall that extends from the sidewall to define a gel receptacle cavity sized and configured to receive a gel receptacle of a respective gel distribution module of a gel distribution apparatus of the headgear when the headgear is within the headgear retaining cavity in a folded storage position.

14. The apparatus of claim 10, wherein the headgear is configured such that all gel distribution modules of the gel distribution apparatus have their gel receptacles within a respective gel receptacle cavity of a respective one of the recesses when the headgear is within the headgear retaining cavity in the folded storage position.

15. A method of storing headgear comprising:
providing headgear having a flexible body and a gel distribution apparatus attached to the body;
folding the body of the headgear to position the headgear in a folded storage position;
positioning the headgear in the folded storage position within a headgear retaining cavity of a case of a storage device such that each gel receptacle of the gel distribution apparatus is within a respective gel receptacle cavity of the case when the headgear is in the folded storage position and is within the headgear retaining cavity; and
closing the storage device.

16. The method of claim 15, comprising:
positioning the storage device having the headgear within the headgear retaining cavity in a remote distribution device.

17. The method of claim 16, comprising:
receiving payment for the headgear via an interface of the remote distribution device; and
in response to receiving the payment, the remote distribution device permitting the storage device having the headgear within the headgear retaining cavity to be removed from the remote distribution device.

18. The method of claim 17, comprising:
manipulating an output mechanism of the remote distribution device; to remove the remote distribution device.

19. The method of claim 18, wherein the case includes a plurality of gel receptacle recesses having gel receptacle cavities in a floor of the case.

20. The method of claim 19, wherein the case includes a plurality of gel receptacle recesses having gel receptacle cavities in at least one sidewall of the case.

\* \* \* \* \*